United States Patent [19]
Koch

[11] Patent Number: 4,483,771
[45] Date of Patent: Nov. 20, 1984

[54] MULTI-LAYER FILTER

[76] Inventor: Elizabeth Koch, 16 Edward St., Demarest, N.J. 07627

[21] Appl. No.: 521,266

[22] Filed: Aug. 8, 1983

[51] Int. Cl.³ .............................................. B01D 25/08
[52] U.S. Cl. ................................. 210/490; 210/500.2; 210/501; 210/504; 210/506
[58] Field of Search ................... 210/500.1, 501, 502.1, 210/503–509, 500.2, 483, 484, 488–492, 496

[56] References Cited

U.S. PATENT DOCUMENTS

| | | | |
|---|---|---|---|
| 3,327,859 | 6/1967 | Pall | 210/266 |
| 3,544,457 | 12/1970 | Tulley et al. | 200/500.1 |
| 3,996,141 | 12/1976 | Updike | 210/501 |
| 4,032,457 | 6/1977 | Matchett | 210/501 |

OTHER PUBLICATIONS

Catalog, Gelman Sciences, Inc., Medical Div., 4/81, PB400A.
Filtration Catalog—Nuclepore Corp., No. 50, p. 17.
Catalog No. 82, Micro Filtration Systems, p. 24.

Primary Examiner—Ivars Cintins
Attorney, Agent, or Firm—Collard, Roe & Galgano

[57] ABSTRACT

A multi-layer filter combination having a macrofilter layer with a predetermined thickness and two major sides including porous material impregnable with bacteria-destroying medication and having pore sizes in the range from about 1 micron to about 120 microns. There is also a microfilter layer having a prearranged thickness smaller than the thickness of the macrofilter and including a porous membrane having pore sizes from about 0.1 micron to about 10 microns. The microfilter layer is mechanically bonded to at least a major side of the macrofilter layer, whereby inhibiting transfer of any remaining live bacteria which may have survived exposure to the bacteria-destroying medication, and which may attempt to pass outwardly beyond the microfilter layer. The medication is either an antibiotic and an iodophore.

18 Claims, 2 Drawing Figures

MULTI-LAYER FILTER

FIELD OF THE INVENTION

This invention relates to a multi-layer filter containing bacteria-destroying medication to prevent passage of bacteria which may be contained in a liquid from passing, during the flow of the liquid, beyond the multi-layer filter.

DESCRIPTION OF THE PRIOR ART

Filtering of liquids to remove particles of various sizes and to retain bacteria are known. In Grossman, U.S. Pat. No. 3,742,946, an elongated filter is disclosed that is used for dialysis. In this patent, there are provided a diversity of semi-permeable membranes which are designed to pass bodies having a relatively low molecular weight, while retaining bodies of a higher molecular weight. The membrane is designed to pass water, decomposition products of protein, salt and other inorganic salts present in excessive amounts in blood, as well as drugs such as barbiturates. The membranes are made of regenerated cellulose and other organic ingredients and extends through the length of the filter. Behind the membrane is a solid treating agent which can consist of a solid desiccant for removing water. There is no teaching in this reference of the use of any anti-bacterial agent to be located in semi-permeable membrane.

In the U.S. Pat. No. 3,396,727 to Mount, there is disclosed a filter with an anti-bacterial preventive material. Mount provides a filter housing consisting of paper and an anti-bacterial substance provided in the filter. This filter is used for a catheter in the urinary tract, but does not consist of a porous material which is secured to a membrane filter, as in the present invention.

Updike, U.S. Pat. No. 3,996,141, describes another semi-permeable membrane which can also be used for blood purification and removal of bacteria. This is a single-layer filter, but manufactured by placing, for example, potassium permanganate on one side of the filter, and sodium iodide on the other side to cause a diffusion of the two solutions so that a catalyst is formed—namely, manganese dioxide, inside the filter. Thus, if hydrogen peroxide is placed on one side of the filter, the hydrogen peroxide will be converted to oxygen and water by its reaction through the filter with the blood. Hydrogen peroxide is known as an anti-bacterial agent. Updike does not, however, use a multi-layer filter combination, as used in the present invention, where a macrofilter layer is impregnated with bacteria-destroying medication, and where a microfilter layer is bonded to the macrofilter layer. Updike's sodium iodine is not used as a bacteria-destroying medication, but merely to form a catalyst with potassium permanganate in the manner described.

SUMMARY OF THE INVENTION

It is accordingly an object of the present invention to obviate the disadvantages of the prior art and to devise a multi-layer filter combination which provides a greater safety to blocking the passage of bacteria than the bacteria-retaining filters of the prior art, which does not require any gaskets, and which is strong and is not easily susceptible to breakage, and has sufficient contamination holding capacity.

This object is attained in a multi-layer filter combination which includes a macrofilter layer which has a predetermined thickness and two major sides. The macrofilter layer includes porous material which may be impregnated with bacteria-destroying medication and has pore sizes in the range from about 1 micron to about 120 microns. A microfilter layer, having a smaller thickness, includes a porous membrane having pore sizes from about 0.1 micron to about 10 microns, is mechanically bonded to one surface of the macrofilter, so that any transfer of any remaining live bacteria which may have survived exposure to said bacteria-destroying medication, and which may attempt to pass outwardly beyond said microfilter layer is inhibited.

BRIEF DESCRIPTION OF THE DRAWINGS

Other objects and features of the present invention will become apparent from the following detailed description when considered in connection with the accompanying drawings which disclose illustrated embodiments of the invention. It is to be understood that the drawings are designed for the purpose of illustration only, and are not intended as a definition of the limits of the scope of the invention. In the drawings, wherein similar reference numerals denote similar elements through the several views.

DESCRIPTION OF THE PREFERRED EMBODIMENTS

Figure 1:
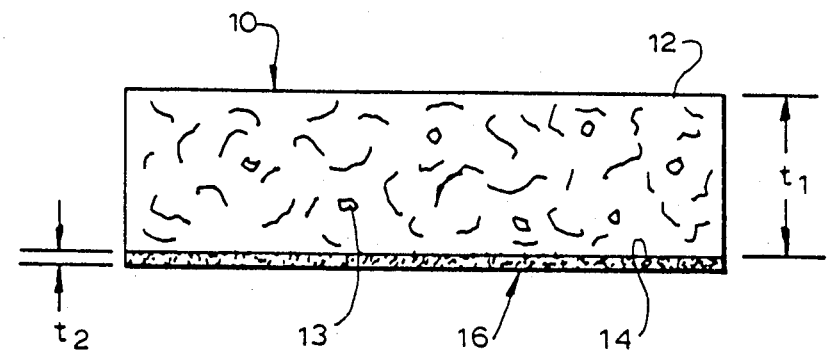
FIG. 1 is a cross-section through a first embodiment of the multi-layer filter combination, according to the present invention.

Referring now to the drawings, there will be seen in FIG. 1 a macrofilter layer 10 of a predetermined thickness "$t_1$" and having a major side 12 and another major side 14. Macrofilter layer 10 will generally consist of porous material which may be impregnated with bacteria-destroying medication 13, such as antibiotics or iodine. The pore size of macrofilter layer 10 will generally range from 1 micron to about 120 microns. A microfilter layer 16 which has a thickness $t_2$ smaller than the thickness $t_1$ is composed of a porous membrane which has pore sizes ranging from about 0.1 micron to about 10 microns. Microfilter layer 16 is advantageously mechanically bonded to one of the major sides of macrofilter layer 10, and in the example shown, to major side 14 of macrofilter layer 10. The bonding takes place along portions of at least one major side of the microfilter layer juxtaposed with at least portions of the major side of the macrofilter layer. In this manner, any live bacteria that travels through macrofilter layer 10 to microfilter layer 16 will be substantially destroyed by the bacteria-destroying medication.

In a preferred version of the invention the thickness $t_2$ of microfilter layer 16 is about 0.005 inches, and its porous membrane includes a unitary organic resin film having pore sizes in the range from about 0.1 microns to about 10 microns. Resin film 16 may have random and irregular passages therethrough of sufficiently small dimensions to block the passage of any bacteria which may have survived exposure to bacteria-destroying medication 13.

In the embodiment shown in FIG. 1, major side 12 and major side 14 of macrofilter layer 10 has a width and length substantially identical to the width and length of each major side of microfilter layer 16. Macrofilter layer 10 is bonded to the microfilter layer 16 along juxtaposed major sides thereof, and in a preferred manner, microfilter layer 16 is coated onto the macrofilter layer 10. It is also possible that part of the macrofilter could be covered with a microfilter having a variable pore size.

Figure 2:
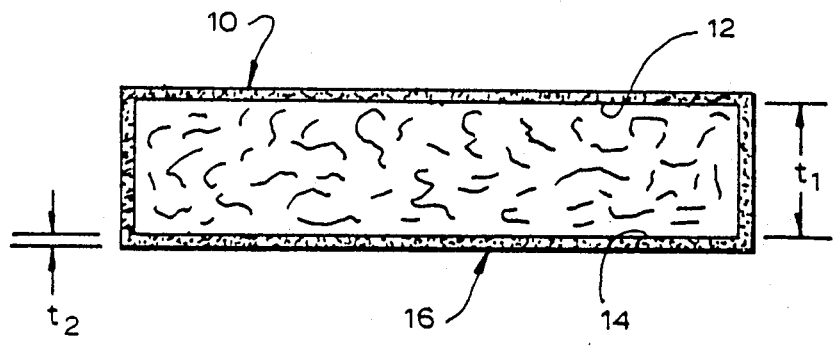
FIG. 2 is a cross-section of a second embodiment of the multi-layer filter combination, according to the present invention.

In a second embodiment of the invention, shown in FIG. 2, microfilter layer 16 is likewise bonded to the macrofilter layer 10 by being coated thereon. In this second embodiment, microfilter layer 16 completely and tightly envelopes macrofilter layer 10. Macrofilter layer 10 may be composed of either synthetic plastic material, or of non-plastic material. Suitable synthetic plastic materials are, for example, polyethylene, polypyropropylene, nylon and teflon. A suitable non-plastic material, for example, is charcoal. Microfilter layer 16 can be supplied in any suitable size or shape. Macrofilter layer 10 may be intrinsically made hydrophobic (water-repellant) or hydrophilic (absorbing water). The water-repellant type will preferably be used where gases are to be filtered, while the water-absorbing type will be used where liquids need to be filtered. In a preferred embodiment, macrofilter layer 10 forms a substrate for the microfilter layer 16. Macrofilter layer 10 can be impregnated with any aqueous or powdered bacteria-destroying material, for example antibiotics, such as penicillin, iodine, tetracyclene, kanamycin, or sulfonamides or any of a host of bacterial destroying materials.

Microfilter layer 16 may be composed of synthetic plastic material, for example of cellulose triacetate, polyester, cellulose esters, polyvinyl chloride, copolymers of polyvinyl chloride, polytetrafluroethylene, an acrylic copolymer, or regenerated cellulose. The material may also be an acetal resin sold under the trademark Delrin (a trademark of E. I. Du Pont de Nemours and Company) or polyvinyl difluoride. Because macrofilter layer 10 can be supplied at any depth or thickness, its prefiltering capacity can be selected to be greater than any currently commercially available material. As microfilter layer 16 is bonded to macrofilter layer 10, the multilayer filter combination is strong and not easily susceptible to breakage.

The multilayer filter combination, according to the present invention, can be effectively used in many areas. Where the fluid is a gas, and, for example, sterile air is required, it is suitable for use in respiratory equipment, in nebulizers or atomizers, as an oxygen filter, in kidney dialysis, and in cardio-pulmonary applications as a by-pass filtering element. Additionally, it can be used in industrial applications, for example in gas chromatography, or in mediastinal sump drainage. Where the fluid is a liquid, and microfiltration is required, it will be found suitable for filtration of an intravenous solution, filtration of solutions used for peritoneal dialysis, filtration of liquids use for irrigation purposes, and filtration of pharmaceutical-grade solutions.

While only a few embodiments have been shown and described, it is obvious that many changes and modifications may be made thereunto without departing from the spirit and scope of the invention.

What is claimed is:

1. A multilayer filter combination, comprising
   a macrofilter layer having a predetermined thickness and two major sides, said macrofilter layer including porous material impregnated with bacteria-destroying medication and having pore sizes in the range from about 1 micron to about 120 microns, and
   a microfilter layer having a prearranged thickness smaller than said predetermined thickness, and including a porous membrane having pore sizes from about 0.1 micron to about 10 microns, said microfilter layer being mechanically bonded to at least a major side of said macrofilter layer, whereby transfer of any remaining live bacteria which may have survived exposure to said bacteria-destroying medication, and which may attempt to pass outwardly beyond said microfilter layer is inhibited.

2. A multilayer filter combination as claimed in claim 1, wherein said bacteria-destroying medication is selected from the group consisting of antibiotics and an iodophore.

3. The multilayer filter combination as claimed in claim 2, wherein said bacteria-destroying medication is aqueous.

4. The multilayer filter combination as claimed in claim 2, wherein said bacteria-destroying medication is powdered.

5. The multilayer filter as claimed in claim 2, wherein said antibiotics are selected from a group consisting of penicillin, tetracyclene, kanamycin, and sulfonamides.

6. A multilayer filter combination as claimed in claim 1, wherein said predetermined thickness is about 0.005 inches, and wherein said porous membrane of said microfilter layer includes a unitary organic resin film having pore sizes in the range from about 0.1 microns to about 10 microns, and formed with random and irregular passages therethrough.

7. The multilayer filter as claimed in claim 1, wherein said macrofilter layer is a substrate for said microfilter layer.

8. A multilayer filter as claimed in claim 1, wherein said microfilter layer is bonded to said macrofilter layer by being coated thereon.

9. A multilayer filter as claimed in claim 1, wherein said microfilter layer completely and tightly envelops said macrofilter layer.

10. A multilayer filter as claimed in claim 1, and wherein said microfilter layer is composed of a synthetic plastic material.

11. A multilayer filter as claimed in claim 10, wherein said synthetic plastic material consists of a material selected from the group of cellulose triacetate, cellulose esters, polyvinyl chloride, copolymers of polyvinyl chloride, acrylic polymer, polytetrafluroethylene, and regenerated cellulose.

12. A multilayer filter as claimed in claim 10, wherein said synthetic plastic material consists of a material selected from the group of nylon, polyester, or any membrane forming material.

13. A multilayer filter as claimed in claim 10, wherein said synthetic plastic material consists of a material selected from the group consisting of an acetal resin and polyvinyl difluoride.

14. A multilayer filter as claimed in claim 1, wherein said macrofilter layer is composed of synthetic plastic material.

15. A multilayer filter as claimed in claim 14, wherein said synthetic plastic material is selected from the group consisting of polyethylene, polypropylene, nylon, and teflon.

16. A multilayer filter as claimed in claim 1, wherein said macrofilter layer is composed of charcoal.

17. A multilayer filter as claimed in claim 1, wherein said microfilter layer is hydrophobic.

18. A multilayer filter as claimed in claim 1, wherein said microfilter layer is hydrophilic.

* * * * *